US005595745A

United States Patent [19]

Znaiden et al.

[11] Patent Number: 5,595,745

[45] Date of Patent: Jan. 21, 1997

[54] PETROLEUM BUTTER

[75] Inventors: Alexander P. Znaiden, Trumbull; Walter Rose, Haven; Michael C. Cheney, Fairfield, all of Conn.

[73] Assignee: Chesebrough-Pond's USA Co., Division of Conopco, Inc., Greenwich, Conn.

[21] Appl. No.: 484,227

[22] Filed: Jun. 7, 1995

[51] Int. Cl.[6] ................................ A61K 7/00; A61K 7/48

[52] U.S. Cl. ........................................... 424/401; 424/70.1

[58] Field of Search .................................... 424/401, 70.1

[56] References Cited

U.S. PATENT DOCUMENTS

| | | | |
|---|---|---|---|
| 3,728,447 | 4/1973 | Osipow | 424/70 |
| 4,198,311 | 4/1980 | France | 252/117 |
| 4,303,543 | 12/1981 | Mansy | 252/117 |
| 4,424,820 | 1/1984 | Cannell | 132/7 |
| 5,002,680 | 3/1991 | Schmidt | 252/90 |
| 5,078,991 | 1/1992 | Birtwistle | 424/70 |
| 5,407,678 | 4/1995 | Rose et al. | 424/401 |
| 5,427,772 | 6/1995 | Hagan | 424/59 |
| 5,441,671 | 8/1995 | Cheney | 252/549 |

FOREIGN PATENT DOCUMENTS

| | | |
|---|---|---|
| 0572271 | 5/1993 | European Pat. Off. . |

*Primary Examiner*—Sallie M. Gardner
*Attorney, Agent, or Firm*—Milton L. Honig

[57] ABSTRACT

A cosmetic composition is provided whose major component is petroleum jelly and incorporates a $C_{18}$–$C_{30}$ acyl lactylate. Most preferred is behenoyl lactylate. Relatively nongreasy and easily spreadable compositions result which have improved skin healing, moisturization and other skin benefit properties.

4 Claims, No Drawings

PETROLEUM BUTTER

BACKGROUND OF THE INVENTION

1. Field of the Invention

The invention relates to cosmetic compositions whose major component is petroleum jelly incorporating additives achieving a product with the consistency of butter to allow for a smooth aesthetic application onto human skin.

2. The Related Art

Petroleum jelly is one of the oldest skin treatment products still in commerce today. For over 100 years, the Chesebrough Company and its successors have sold the substance under the brand, Vaseline®. There is good reason for the longevity of this product. Its occlusive and healing properties render this product especially efficacious against dry and damaged skin.

Of course there are many drawbacks to petroleum jelly. This substance is greasy. When in contact with clothes or anything else, the product has a tendency to be transferred through rub off. An approach to this problem is found in U.S. Pat. No. 5,407,678 (Rose et al.) which employs aluminum starch octenylsuccinate and a $C_{12}$–$C_{15}$ alkyl lactate to provide a nongreasy yet efficacious product form reported active against dry skin.

Another problem with traditional petroleum jelly is its rather stiff consistency. Pure petroleum jelly is not readily spreadable onto the skin surface.

Accordingly, it is an object of the present invention to provide a cosmetic composition with a substantial amount of petroleum jelly that has improved aesthetic properties.

Another object of the present invention is to provide a cosmetic composition with a substantial amount of petroleum jelly that is spreadable onto the skin with a butterlike consistency.

Another object of the present invention is to provide a cosmetic composition with a substantial amount of petroleum jelly having butterlike consistency but leaving relatively little greasy residue after application onto the skin.

Still another object of the present invention is to provide a cosmetic composition with a substantial amount of petroleum jelly capable of moisturizing and conditioning skin as well as removing dead skin.

Yet another object of the present invention is to provide a cosmetic composition with a substantial amount of petroleum jelly that achieves skin healing, imparts anti-aging, anti-wrinkling and skin lightening effects as well as other improved functional activities.

These and other objects of the present invention will become more readily apparent from consideration of the following summary and detailed description.

SUMMARY OF THE INVENTION

A cosmetic composition is provided that includes:

(i) from 50% to 98% by weight of petroleum jelly; and (ii) from 0.01 to 45% by weight of a $C_{18}$–$C_{30}$ acyl lactylate salt.

The most preferred lactylate according to the present invention is behenoyl lactylate.

DETAILED DESCRIPTION OF THE INVENTION

Now it has been found that cosmetic compositions with substantial amounts of petroleum jelly can have their aesthetic properties improved through incorporation of $C_{18}$–$C_{30}$ acyl lactylate salts. Particularly effective are the behenoyl lactylate salts.

Accordingly, a first essential element of the present invention is that of petroleum jelly. Amounts of this material may range from 50% to 98%, preferably from 60% to 90%, optimally from 70% to 85% by weight.

A second essential element of the present invention is that of a $C_{18}$–$C_{30}$, especially $C_{20}$–$C_{30}$, acyl lactylate salt. Most preferred is behenoyl lactylate salt, especially sodium behenoyl lactylate. Suitable cations to form the lactylate salt are those selected from the alkali metal, alkaline earth metal, ammonium and $C_2$–$C_{12}$ alkanolammonium cations. Lactylates of this invention may be polymerized to any degree, but preferably range from 1 to 10, optimally 1 to 3 in degree of polymerization. Acyl lactylate salts are commercially available from the C.J. Patterson Division of RITA Corporation. Amounts of the acyl lactylate salts will range from 0.01 to 45%, preferably from 1 to 40%, more preferably from 10 to 35%, even more preferably from 15 to 30%, optimally from 20 to 28% by weight. The term "anhydrous" encompasses up to 0.5% water.

Petroleum jelly and the acyl lactylate may be present in relative weight proportions of 15:1 to 1.5:1, preferably from 8:1 to 2:1, more preferably from 4:1 to 2.5:1, optimally from 3.5:1 to 2.8:1.

Although compositions according to the present invention may be anhydrous, they usually will contain water in amounts from 0 to 15%, preferably from 0.8 to 10%, optimally from 1 to 8%, especially from 4 to 6% by weight.

Beyond the aforementioned components, the present invention may also include other ingredients typically found in cosmetic formulations. Among these ingredients are emollients, humectants, thickeners, preservatives, fragrances and vitamins.

Emollients may be selected from materials such as $C_8$–$C_{30}$ fatty alcohols, triglyceride oils, silicone oils and a variety of esters. Amounts of the emollients may range from 0.5 to 20%, preferably from 1 to 10%, optimally from 2 to 8% by weight. Illustrative emollients are stearyl alcohol, cetyl alcohol, isopropyl palmitate, isopropyl myristate, lanolin, sunflower oil, evening primrose oil, soybean oil, dimethicone, cyclomethicone, dimethicone copolyol and dimethyl polysiloxane. Particularly preferred emollients include soya sterol, especially soya sterol ethoxylated with from 1 to 5 moles ethylene oxide, and lecithin.

Powdered thickeners may be such materials as chalk, talc, Fullers earth, kaolin, starch, colloidal silica, smectite clays, montmorillonite clays and chemically modified magnesium aluminum silicates.

Among the preservatives useful are methyl paraben, propyl paraben, EDTA salts, potassium sorbate, potassium benzoate and DMDM hydantoin.

Cosmetic compositions of the present invention may also contain vitamin ingredients such as Vitamin A palmitate, Vitamin E acetate, Niacin, Vitamin C and combinations thereof.

Emulsifiers may also be useful for purposes of the present invention. These emulsifiers may be alkoxylated $C_8$–$C_{30}$ fatty acids and fatty alcohols. Examples of such materials are polyoxyethylene (4) lauryl ether, polyoxyethylene (8) monostearate, polyoxyethylene (10) cetyl ether and polyoxyethylene (20) stearyl ether.

The following examples will more fully illustrate select embodiments of this invention. All parts, percentages and proportions referred to herein and in the appended claims are by weight of the total composition unless otherwise stated.

EXAMPLE 1

The following formulation was prepared as illustrative of cosmetic compositions according to the present invention.

TABLE I

| COMPONENT | WEIGHT % |
|---|---|
| Petroleum Jelly | 77.5 |
| Behenoyl Lactylate | 22.5 |

The above ingredients were weighed into a reactor. Heat was applied with mixing until the resultant composition was totally liquid and uniform. The composition was then transferred to a Barinco Homogenizer and subjected to thirty minutes of homogenization at 40–45 rpm. A highly smooth product resulted which did not feel greasy to the touch.

EXAMPLES 2–10

A further series of formulations according to the present invention are described in Table II.

TABLE II

| | EXAMPLE (WT. %) | | | | | | | | |
|---|---|---|---|---|---|---|---|---|---|
| COMPONENT | 2 | 3 | 4 | 5 | 6 | 7 | 8 | 9 | 10 |
| Petroleum Jelly | 85 | 75 | 90 | 85 | 85 | 70 | 70 | 70 | 70 |
| Behenoyl Lactylate | 15 | 25 | 10 | — | — | 15 | 15 | — | 30 |
| Stearoyl Lactylate | — | — | — | 15 | — | 15 | — | 30 | — |
| Isostearoyl Lactylate | — | — | — | — | 15 | — | 15 | — | — |

Each of the examples are processed similar to that of Example 1. Most effective in physical and performance properties will be Examples 2, 3 and 10 containing the behenoyl lactylate.

The foregoing description and Examples illustrate selected embodiments of the present invention and in light thereof various modifications will be suggested to one skilled in the art, all of which are within the spirit and purview of this invention.

What is claimed is:

1. A cosmetic composition comprising:

(i) from 50% to 98% by weight of petroleum jelly; and (ii) from 10 to 40% by weight of a behenoyl lactylate salt.

2. A composition according to claim 1 wherein the behenoyl lactylate is present in an amount from 15 to 30% by weight.

3. A composition according to claim 2 wherein the behenoyl lactylate is present in an amount from 20 to 28% by weight.

4. A composition according to claim 1 which is anhydrous.

* * * * *